United States Patent [19]
Ilbawi et al.

[11] Patent Number: 5,326,374
[45] Date of Patent: Jul. 5, 1994

[54] BODY-IMPLANTABLE DEVICE FOR CONTROLLING THE SIZE OF A FLUID PASSAGEWAY

[75] Inventors: Michel N. Ilbawi, 1917 Midwest Club, Oak Brook, Ill. 60521; James E. Colgate, Evanston, Ill.; David A. Johnson, Evergreen Park, Ill.

[73] Assignee: Michael N. Ilbawi, Oak Brook, Ill.

[21] Appl. No.: 983,658

[22] Filed: Dec. 1, 1992

[51] Int. Cl.$^5$ .................................. A61M 1/10
[52] U.S. Cl. ........................ 623/3; 137/624.15
[58] Field of Search ............... 623/3; 600/16; 251/129.04, 208; 137/624.15

[56] References Cited
U.S. PATENT DOCUMENTS

| | | | |
|---|---|---|---|
| 3,860,968 | 1/1975 | Shapiro | 623/3 |
| 4,599,081 | 7/1986 | Cohen | 623/3 |
| 5,169,381 | 12/1992 | Snyders | 600/16 |
| 5,192,311 | 3/1993 | King et al. | 623/1 |

*Primary Examiner*—Jerome L. Kruter
*Attorney, Agent, or Firm*—Allegretti & Witcoff

[57] ABSTRACT

A body-implantable device for controlling the size of a fluid flow passageway within the body, typically for use in a Fenestrated Fontan operation. A housing is provided and secured within the body, typically to the artificial septum sutured into place in the Fontan operation. A flow passageway extends through the housing. An antenna is responsive to electromagnetic signals emitted from outside the body and conveyed through the body without wires to the antenna. Means are provided for varying the cross-section of the flow passageway in a manner responsive to signals received by the antenna.

17 Claims, 4 Drawing Sheets

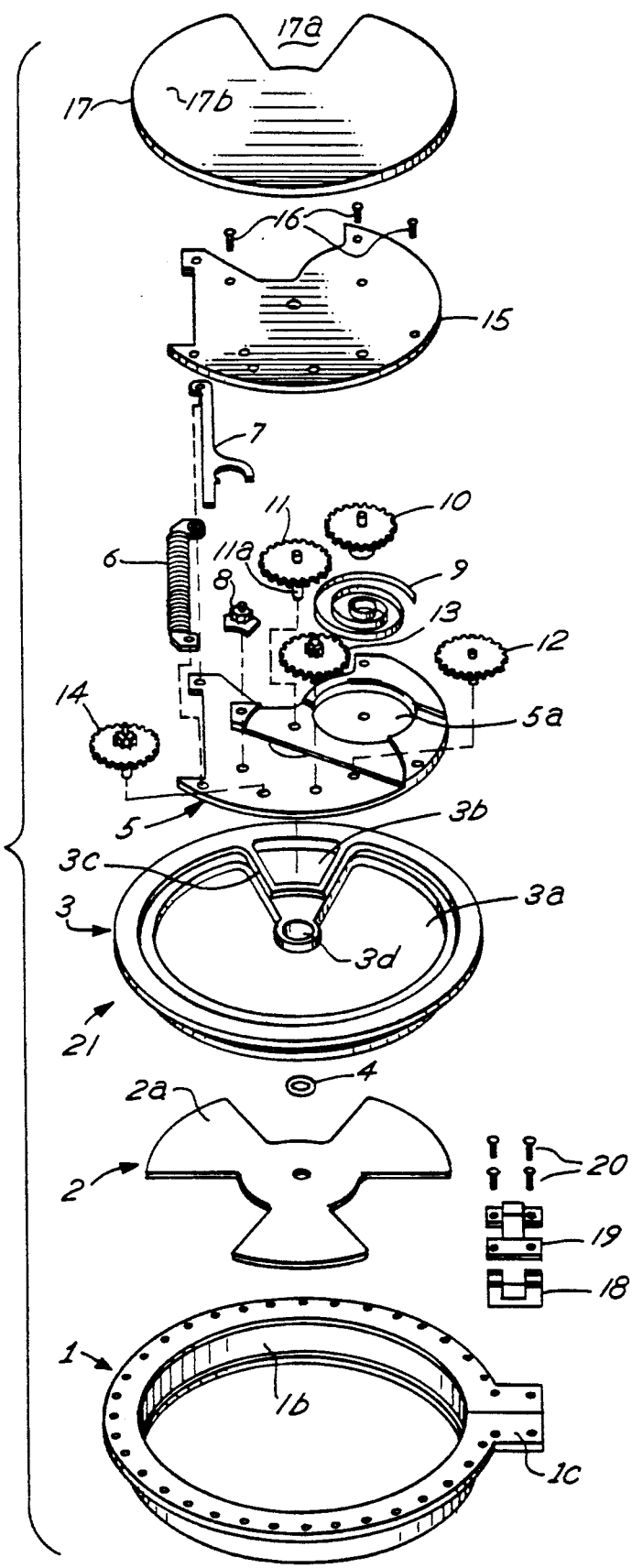

BODY-IMPLANTABLE DEVICE FOR CONTROLLING THE SIZE OF A FLUID PASSAGEWAY

BACKGROUND OF THE INVENTION

This invention relates to a body implantable device which controls the size of a fluid flow passageway within the body, controllable from outside of the body without any direct physical connection to a control unit outside of the body.

In surgery, there may be a need for controlling, for example, the cross-sectional area of the pulmonary artery in a pulmonary arterial banding procedure. There also is a need to control the size of an atrial fenestration in the Fontan operation. Both of the above procedures are well known.

Referring to the latter procedure, the Fontan operation is performed for physiologic correction of a congenital heart condition where there is only one pumping chamber. The principle of the procedure is that blood is propelled from the right upper chamber to the lungs without the need for the pumping action of the right lower chamber or ventricle.

To accomplish this, a right atrium is isolated through the use of a septation patch made of a synthetic material such as GORETEX PTFE sheeting. Then, the isolated right atrium is connected to the pulmonary artery. In this way, the blood flows from the body to the right atrium and directly to the pulmonary arteries. The blood then passes to the left atrium, and from there is pumped into the body.

The blood flow from the right atrium to the pulmonary arteries, leading to the lungs, is totally passive in this instance, and depends on the kinetic energy supplied by the left side of the heart. As a result, there is a mild degree of blood backup on the right side of the circulation. This causes relative blood stagnation and higher systemic venous pressure, leading to undesirable extravasation of fluids from the vascular system. To counteract this, a fenestration or aperture has been provided to the synthetic septation patch applied to the heart in this operation.

The major determinants of the eventual systemic venous pressure following the Fontan operation include the pulmonary vascular resistance, the left side filling pressure, which depends on the compliance and capacity of the left heart chambers, and the degree of mechanical obstruction to pulmonary arterial blood flow or pulmonary venous return. In most cases, these determinants are abnormal in the immediate postoperative period, and tend to improve with time.

The clinical results of the Fontan procedure are critically dependent on the early and late systemic venous pressure. Markedly elevated venous pressure following surgery leads to significant extravasation of fluids from the vascular system. This results in hypotension, low cardiac output and impaired organ functions. Thus, it is important to have the capacity to intervene in the early-post operative period to assist in causing these determinants to return to normal levels to obtain the best results with the Fontan operation.

The fenestration referred to above serves as an intentional atrial septal defect or hole between the upper two chambers, to reduce pressure on the right side of the circulation for minimization of post operative complications. It is usually desirable to subsequently close this hole when the different hemodynamic parameters immediately after operation return to normal later on in the postoperative period. Such an approach is presently called the Fenestrated Fontan operation, and has yielded excellent results with markedly improved outcome of the most critically sick patients.

There are currently two clinical approaches presently practiced for fenestration in the Fontan operation. One of these approaches comprises leaving a calibrated fenestration opening in the inner atrial patch that is emplaced by the surgeon. Cardiac catheterization is performed before discharge, and a trial occlusion of the fenestration by a balloon is performed. If the patient tolerates the occlusion, the fenestration is closed with an umbrella-like device emplaced by catheter, which hooks to the edge of the fenestration and occludes the opening on an essentially permanent basis.

One problem with this approach is that the size of the fenestration or hole is not adjustable. Thus, if the hole is too big or too small, nothing can be done to adjust its size after the patient is off the cardiopulmonary bypass machine. Also, this procedure requires repeat cardiac catheterization, which of course would be desirably avoided. Also, the umbrella device used in the procedure was withdrawn from the market by the Food and Drug Administration because of breakage in a very small number of instances. Finally, once the fenestration is closed, there is no way to reopen it short of major surgery.

The other approach of Fenestrated Fontan utilizes a similar hole between the upper two chambers in the artificial septum, but uses a "purse string suture" around the hole, with one end of the string lying subcutaneously, outside of the heart. As a disadvantage of this approach, while the hole size can be adjusted by tightening or loosening the string, the adjustments are usually gross and imprecise, and require an incision of the skin and subcutaneous tissue. This, in turn, can lead to a higher instance of infection, especially if it is done on a repeated basis. Hence, this approach is close to an all or nothing situation because the fine adjustments are made only with difficulty and luck.

DESCRIPTION OF THE INVENTION

In accordance with this invention, an implantable device provides a controlled cross-sectional opening between the two upper chambers of the heart in the case of the Fontan operation, although analogous devices in accordance with this invention many be used in other surgical procedures as well. By this invention, the device is totally implantable, and thus is less predisposed to infection. In preferred embodiments, the device can precisely provide a desired cross section of a flow passageway, which is easily adjusted by means controlled from the outside without a direct wire or other material connection leading through the skin. This control may be accomplished without further catheterization or surgical procedures. Thus, in the Fontan procedure, the physician can achieve an optimal opening diameter between the two chambers created by the artificial septum, and this opening may be adjusted on practically a routine basis for the benefit of the patient as needed.

By this invention, a body-implantable device is provided for controlling the size of a fluid flow passageway within the body. The device comprises a housing, plus means for securing the housing within the body. A flow passageway is provided, extending through the housing. Signal receiving means are provided, responsive to electromagnetic signals emitted from outside the body and conveyed through the body without wires to the signal receiving means. Means are also provided for varying the cross-section of the flow passageway in a manner responsive to signals received by the signal receiving means.

The securing means may preferably comprise a perforated flange for suturing to the body, or a suture cuff, for example. Specifically, in the Fontan procedure, the perforated flange may be sutured to the artificial septum which is emplaced within the heart by the procedure.

The means for varying the cross section of the flow passageway may comprise a blade which is capable of moving transversely across the flow passageway to vary the cross-section as the blade so moves between various positions, so that the cross-section may be small or large, depending upon the position of the blade. The blade may press against a seal to reduce leakage of fluid around the blade, if desired.

Specifically, the means for varying the cross-section of the flow passageway may comprise a rotatable shaft, and a plurality of blades mounted on the shaft in transverse relation to the passageway. The blades are rotationally spaced about the shaft with spaces between the blades of typically at least substantially the fully-opened cross-sectional size of the flow passageway. Accordingly, rotation of the shaft causes the blades to sequentially occlude the flow passageway, to vary the cross section thereof.

Thus, if the shaft rotates in only a single direction and the surgeon finds that the blade has moved too far to occlude too much of the passageway, the shaft may be further rotated by the surgeon to cause the occluding blade to clear the flow passageway and for a second blade to enter into engagement with the flow passageway, for another opportunity to adjust the passageway size.

The above shaft may be rotated by spring driven gear means, similar to a watch mechanism, with the control of such rotation being provided by the signal receiving means.

DESCRIPTION OF THE DRAWINGS

FIG. 4 is an exploded perspective view of the device shown in FIG. 3;

DESCRIPTION OF SPECIFIC EMBODIMENTS

Figure 1:
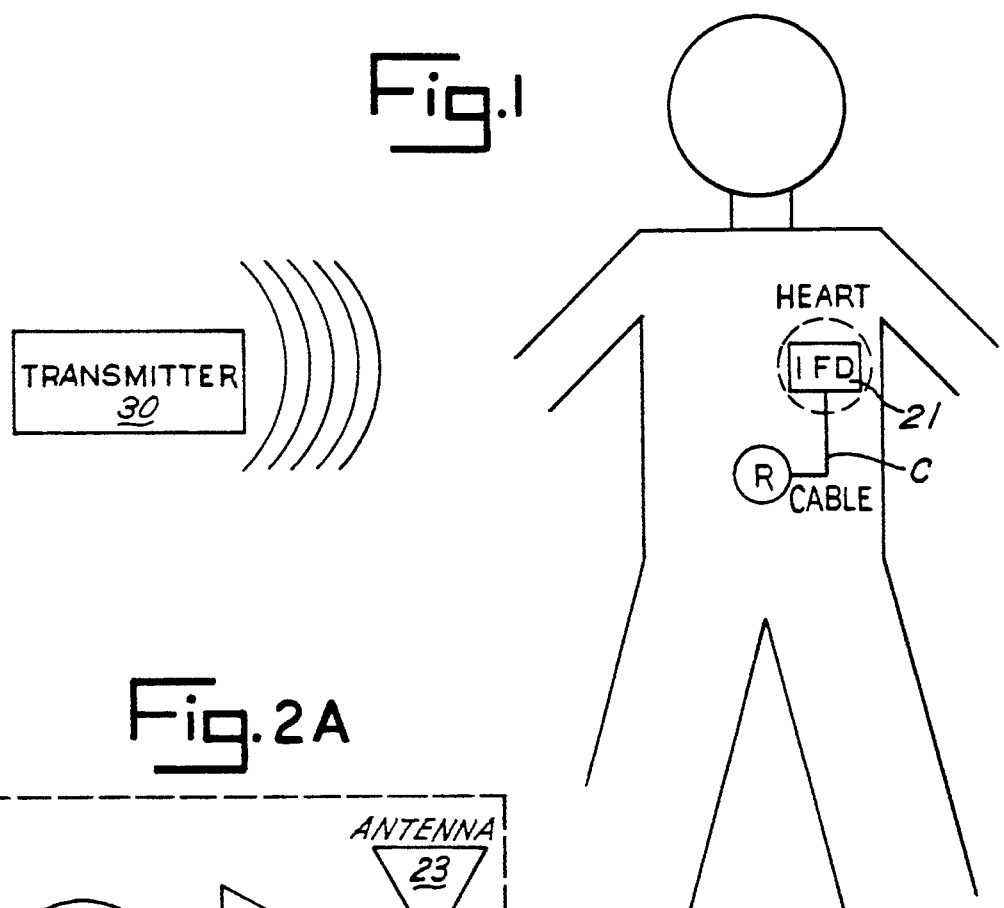
FIG. 1 is a diagrammatic view of the body implantable device of this invention plus a separate transmitter for control thereof, positioned outside of the body.

Referring to the drawings, and especially FIG. 1, a body implantable device for providing an adjustable fenestration in a Fontan operation is disclosed. During the operation, the fenestration device 21 (IFD) is implanted on an artificial membrane which, in turn, is sutured within the heart to form an interatrial patch which has been sewn into the patient by the surgeon in the Fontan operation, to form partially artificial atrial chambers for the heart. The fenestration device 21 within the heart defines a flow passageway extending therethrough between the two atria within the heart which are newly defined by the interatrial patch. As previously stated, the patch, may be made of GORTEX PTFE membrane, or any other desired material. The device 21 connects to receiver R via a cable C, with the device 21, the receiver, and the connecting cable C being completely implanted within or near the chest or abdominal cavity of the patient. Receiver R may be positioned under the skin in a surgically accessible area in the manner similar to the placement of a power supply for a known heart pacemaker.

Then, the transmitter 30 shown in FIG. 1 may send signals, for example at a frequency of 13-14 MHz and specifically 13.8 Mhz, near a theoretical ideal frequency of 13.56 MHz.

Figure 2A:
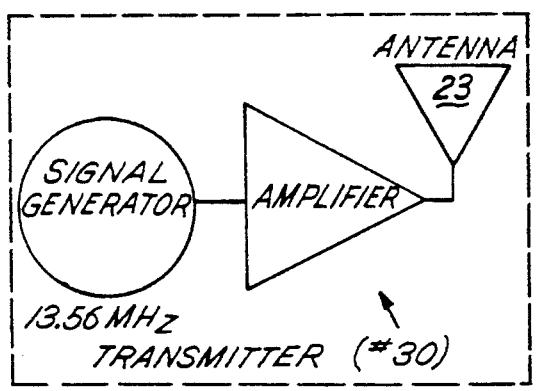
FIGS. 2 and 2A are circuit diagrams of the electronic components of the invention of FIG. 1.
Figure 2:
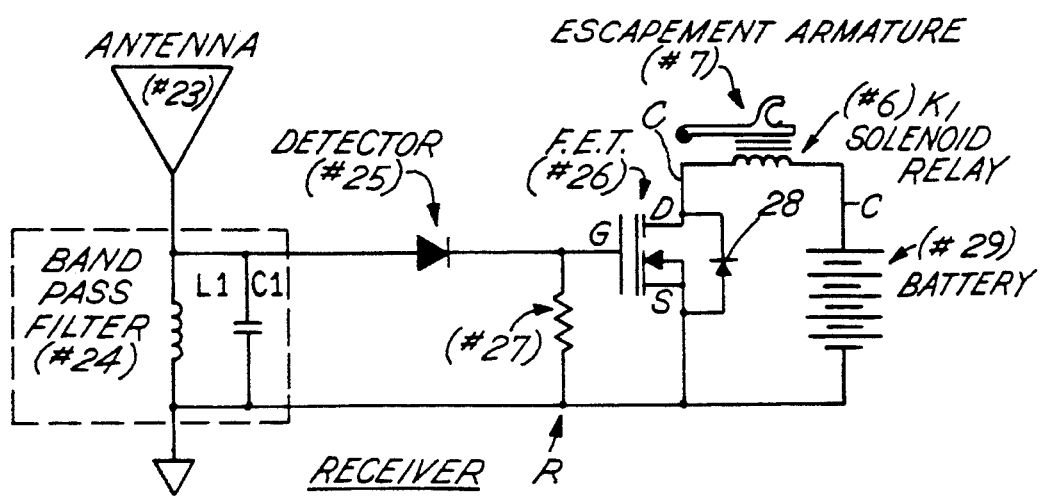
Figure 3:
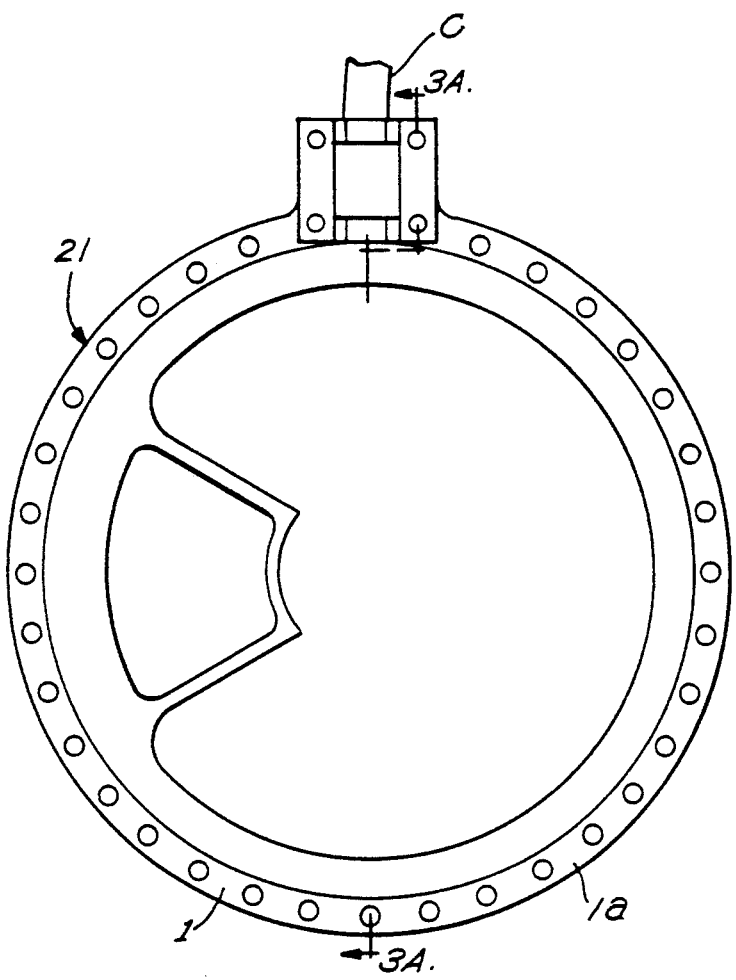
FIG. 3 is a plan view of the implantable fenestration device (IFD) in accordance with this invention, with the implantable receiver and the connecting cable broken away.
Figure 3A:
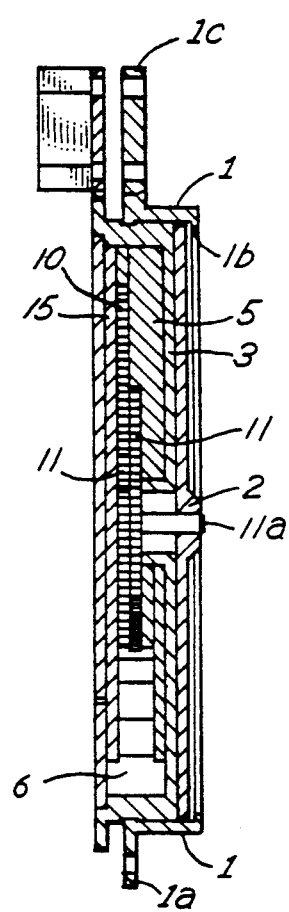
FIG. 3a is a transverse sectional view of the device of FIG. 3 taken along lines 3a—3a of FIG. 3.
Figure 5:
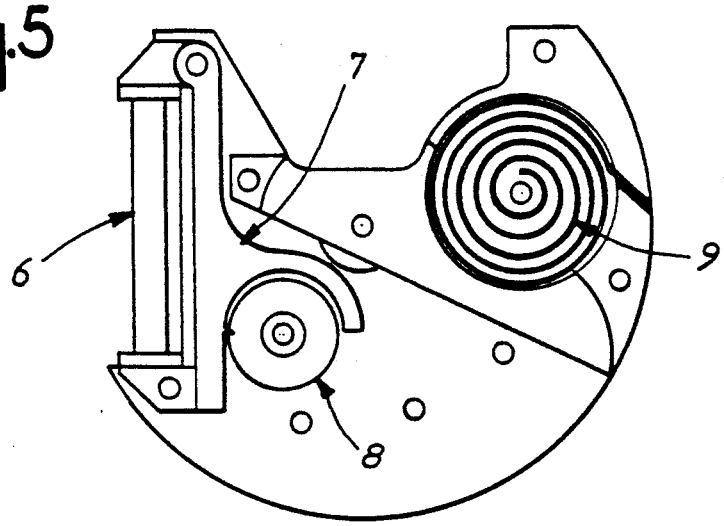
FIG. 5 is a plan view of a subassembly of the device of FIG. 3.
Figure 5A:
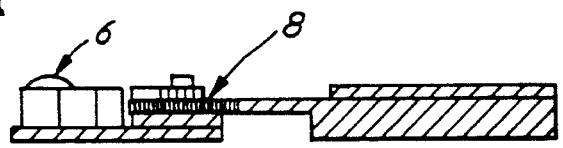
FIG. 5a is an elevational view of the subassembly of FIG. 5.
Figure 6:
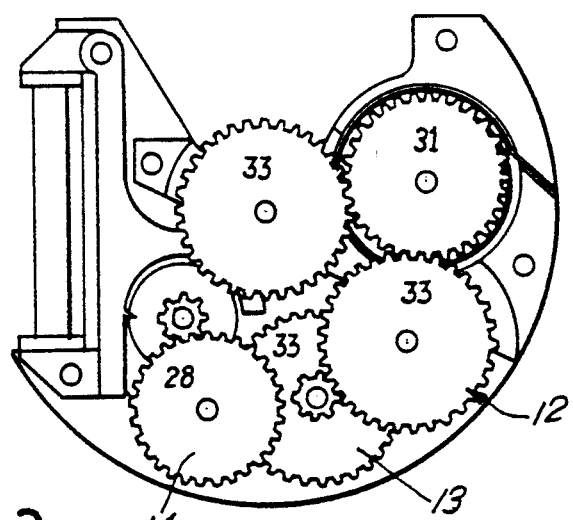
FIG. 6 is a plan view of a subassembly similar to the sub-assembly of FIG. 5 but with more parts added.
Figure 6A:
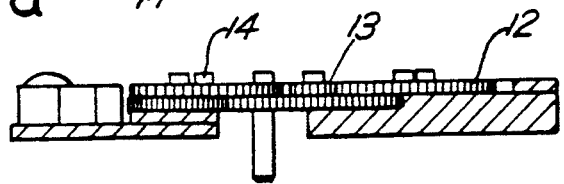
FIG. 6a is an elevational view of the subassembly of FIG. 6.

Transmitter 30 conventionally comprises a signal generator in conjunction with an amplifier and an antenna as in FIG. 2, to emit a signal at a desired frequency, which signal is desirably coded in a conventional manner so that stray signals at that frequency do not cause the implantable fenestration device 21 to adjust the passageway size.

The transmitted signal is received by antenna 23 in the receiver R (FIG. 2), being filtered by filter circuit 24 to prevent false signals from triggering the device. This signal, if valid, is applied to a detector/decoder 25. In turn detector/decoder 25 enables switch 26, which allows current to flow through relay 6. When current flows through solenoid relay 6, it creates a magnetic field which pulls escapement armature 7, allowing fenestration device 21 to vary the cross-section of the flow passageway, as specifically described below. Current is provided by battery 29 to receiver R.

Specifically as shown in FIG. 2, the receiver design is based on an LC filter circuit. This circuit 24 acts as selective filter that reduces the potential for activation by frequencies from other sources. The received signal in the unit is then detected by a germanium or zero bias diode 25, which causes current to flow through an N-channel enhancement field effect transistor 26. Field effect transistor 26 acts as a switch which is open in the absence of current and closed in its presence. Thus, when current flows through it from diode 25, transistor 26 acts as a closed switch, allowing the current to pass from battery 29 to a solenoid including relay 6 and armature 7, to activate the fenestration device 21 for variation of the flow passageway as shown for example in FIG. 4.

Thus, the surgeon can quickly adjust the desired size of the fenestration to meet the patient's needs without performing any incision or any other invasive activity with respect to the patient.

Receiver antenna 23 comprises a pair of sections of, for example, 3.15 meters of 40 AWG magnet wire wrapped approximately 270 turns around a 6.4 centimeter long, 0.6 centimeter air core made of plastic to form a quarter wave helix. Each of these sections are helices which are wrapped starting at each end of the core. They meet at the center where one helix is connected to an LC tank, and the other to the circuit reference ground. The active components of the receiver are all mounted within the antenna.

Antenna 23 then drives an LC bandpass filter which is a single pole filter comprising inductor L1, tuned to resonate by the capacitor C1. The filter output is detected and rectified by diode 25, typically a germanium or zero bias diode.

Such a detector has regularly low diode forward resistance, which makes it preferable to other diode types because of increased sensitivity.

Field effect transistor 26 acts as a switch if it has sufficient current flowing between its gate G and its source S. In such circumstance transistor 26 closes a switch between its source S and drain D. In the absence of input signal, the switch is open.

Resistor 27 is positioned across the gatesource junction of the transistor to clamp it in the off state when no input signal is present. The presence of resistor 27 causes the circuit to require more current to turn the fenestration device 21 on.

Diode 28 across the drain source junction of the field effect transistor 26 protects transistor 26 from the inductive kick-back generated by the relay core.

Typically, battery system 29 can be merely a pair of two 3 volt lithium oxide batteries connected in series.

Relay 6 is located in fenestration device 21 implanted in the heart, being connected to receiver R via implanted cable C.

When the field effect transistor 26 is in the off state, essentially no current can flow from batteries 29 to the relay 6. However, when an input signal is present, preferably a decoded transmitted pulse, field effect transistor 26 is in the on state, which allows current to flow from the batteries 29 in the receiver to relay 6 for activation. By such activation, device 21 is activated to vary the cross-section of its flow passageway.

Referring to FIGS. 3–6, implantable fenestration device 21 is disclosed. Device 21 comprises a circular body 1 which carries a perforated flange 1a for suturing to a septum or the like. Body 1 is ring shaped, and snaps into the lower valve body 3 from both sides of the implanted septum to capture the septum, followed by suturing to flange 1a.

Rotary plate 2 defines blades 2a having outer surfaces that reside in annular groove 1b of attachment ring 1, so that plate 2 will not float free even it if is broken off of its shaft. Ear portion 1c of ring 1 serves as a strain relief for the electrical cable C that connects with receiver R.

Lower valve body 3 comprises a circular housing structure plus a side wall 3a in which an aperture 3b is defined. Aperture 3b is proportioned to be approximately the size and shape of each of the blades 2a of rotary plate 2, but typically slightly smaller so that each blade of rotary plate 2 can completely occlude aperture 3b in the proper rotational position.

An elevated rim 3c is provided about aperture 3b to permit sealing between blade 2a and rim 3c. Also, rim 3c extends about the periphery of valve body 3 for sealing the interior thereof.

O-ring 4 is provided on shaft 11a for sealing through the central aperture 3d of lower valve body, to minimize blood leakage into the interior of the system.

Lower gear case 5 is a structure upon which the gears and springs of the drive system of this apparatus can be mounted. The vertical and horizontal dotted lines show the positioning of the gears and various parts, and the apertures through which their respective shafts project.

Upper gear case 15 cooperates with lower gear case 5 to form a housing for the valve cover drive system. Drive spring 9 fits into circular recess 5a. Also, carried in the system are drive gear 10, through which power is taken off of drive spring 9, valve cover gear 11 which engages drive gear 10. Control gears 12, 13, and 14, help to create a large mechanical advantage for the system. Ratchet wheel 8, and escapement armature 7 function in a conventional manner, with the system making use of conventional wristwatch technology. Relay 6, described above and also shown in FIG. 2, is also shown.

The above entire structure can be assembled into a unit, sandwiched between plates 5, 15, and held there by screws 16. This system, in turn, fits within lower valve body 3, and is sealed by upper valve body 17.

Drive gear 10 connects directly to drive spring 9, engaging drive cover gear 11 as well as control gear 12. In the present embodiment, drive gear 10 has 31 teeth. Valve cover gear 11 connects with shaft 11a, with the shaft connecting to rotary plate 2.

Control gears 12, 13, and 14 serve to reduce the high power level torque of the drive gear to a much lower signal level torque at ratchet wheel 8. This enables a small power input to the relay 6 to control a much larger power release from the drive spring.

Control gear 13 is a compound gear which engages control gear 12 having 33 teeth and an 8 tooth pinion. Control gear 14 is also a compound gear engaging the pinion on ratchet wheel 8, for a high mechanical advantage actuation.

Upper valve body 17 fits in sealing manner into lower valve body 3 with indentation 17a being in alignment with aperture 3d and sealed in hermetic manner, for instance by laser welding, to elevated periphery 3c around the entire circumference of both valve bodies. Small hole 17b is present to receive the relay wires connecting relay 6.

Thus, aperture 3b is open throughout the device 21 to provide a flow passageway extending through the housing. Blades 2a of rotary plate 2 are present to vary the cross section of the flow passageway defined by members 3b and 17a. When signals are received by receiver R, a signal through the cable C causes activation of relay core 6 which, in turn, pulls escapement 7 to the left, allowing ratchet wheel 8 to advance by one tooth. This in turn, through gear train 12, 13, 14 allows drive spring 9 to unwind a small amount, turning valve plate 2 by a small amount, as driven by gear 10, gear 11, and shaft 11a, under control of the signals from transmitter 20. Thus, the position of a blade 2a passing across aperture 3b can be controlled, to control the cross-section of flow passageway 3b. The surgeon is free to control the size of the fenestration between the left and right atria on essentially a moment by moment basis so that the conditions for the patient may remain optimum.

Part of the principle of operation of the device of this invention is similar to that of a spring-wound wrist watch having only one hand. Like a watch, the power source is a wound-up spring which is contained within the body, and the unwinding of the spring is controlled by an escapement. Also, like a watch, a shaft 11a protrudes from the center, but in this case to drive valve plate 2. However, as a major difference from a watch, while a watch hand moves continuously, valve plate 2 rotates only when commanded to. The command to the unit 21 is in the form of a voltage pulse which activates a relay 6 to operate escapement 8, etc., allowing spring 9 to unwind by a single unit of rotation. The unwinding spring drives gears 10, 11 plus central shaft 11a, turning valve plate 2, typically about 1.7 degrees per pulse. Thus, the size of flow passageway 3b, 17a may be carefully and precisely controlled simply by specifying the number of voltage pulses, as controlled from transmitter 20.

The unit 21 of this invention requires only a very small amount of energy to activate relay 6. Thus a small energy input controls the release of a much larger amount of energy from spring 9. This is accomplished by the gear train connecting spring 9 with escapement 8 via gears 12, 13 and 14 to provide a ratio of approximately 40:1. Thus, the gear torque at the ratchet 8, locked in place by escapement 7, may be 40 times less than the gear torque at the spring.

When the relay 6 is activated by the voltage pulse, it disengages escapement 7 from ratchet wheel 8 which begins to turn. The turning of ratchet wheel 8, however, pulls the escapement back into engagement which stops turning after 1/5 of a revolution, if ratchet wheel 8 has 5 sides as shown. As a specific embodiment, fenestration device 21 may be designed to permit one complete rotation of valve plate 2, which provides adjustment of the fenestration from full open to full closed three times and from full closed to full open three times. A larger spring can of course provide more rotation and adjustment capacity.

It may also be desirable to dispense with the implantable receiver connected to member 21 by a cable, and to provide receiver circuitry to unit 21. In this case, if desired, the small amount of power required to operate the relay may be provided by conventional electromagnetic coupling to a source outside of the body.

The blood-contacting surfaces of device 21 of this invention may be conventionally coated and bonded to pyrolytic carbon and/or heparin to suppress clotting.

The above has been offered for illustrative purposes only and is not intended to limit the scope of the invention of this application, which is as defined in the claims below.

That which is claimed is:

1. A body implantable device made of a body compatible material for controlling the size of a fluid flow passageway within the body, which comprises:
   a housing;
   means for securing said housing within the body;
   a flow passageway of unchanging cross-section extending through said housing;
   signal receiving means, responsive to electromagnetic signals emitted from outside the body and conveyed through the body without wires to said signal receiving means; and
   means for changing the cross-section of said flow passageway to another position in a manner responsive to signals received by said signal receiving means.

2. The device of claim 1 in which said securing means comprises a perforated flange for suturing to a septum.

3. The device of claim 1 in which said means for change the cross-section of said flow passageway comprises a blade capable of moving transversely across said flow passageway to vary said cross-section.

4. The device of claim 3 in which said means for change the cross-section of said flow passageway comprises a rotatable shaft, and a plurality of blades mounted on said shaft in transverse relation to said passageway, said blades being rotationally spaced about said shaft, with spaces between said blades of at least substantially the fully-open cross-sectional size of said flow passageway, whereby rotation of said shaft causes said blades to sequentially occlude said flow passageway to vary said cross-section thereof.

5. The device of claim 4 in which said shaft is rotated by spring-driven gear means, controlled by said signal receiving means.

6. The device of claim 1 which is for providing a fenestration in the Fontan operation.

7. The device of claim 1 in which said flow passageway is coated with at least one of pyrolytic carbon and heparin.

8. A body-implantable device made of a body compatible material for providing a fenestration in the Fontan operation for controlling the size of a fluid flow passageway through an artificial intra-atrial septum within the heart, which comprises:
   a housing;
   means for securing said housing to said septum;
   a flow passageway of unchanging cross-section extending through said housing;
   signal receiving means, responsive to electromagnetic signals emitted from outside the body and conveyed through the body without wires to said signal receiving means; and
   means for varying the cross-section of said flow passageway to another normally invariant position in a manner responsive to signals received by said signal receiving means, said means for varying the cross-section of said flow passageway comprising a blade capable of moving transversely across said flow passageway to vary said cross section.

9. The device of claim 8 in which said means for varying the cross-section of said flow passageway comprises a rotatable shaft, and a plurality of blades mounted on said shaft in transverse relation to said passageway, said blades being rotationally spaced about said shaft, with spaces between said blades of at least substantially the fully-open, cross-sectional size of said flow passageway, whereby rotation of shaft causes said blades to sequentially occlude said flow passageway to vary said cross-section thereof.

10. The device of claim 9 in which said shaft is rotated by spring-driven gear means, controlled by said signal receiving means.

11. The device of claim 10 in which said securing means comprises a perforated flange for suturing to a septum.

12. The device of claim 11 in which said flow passageway is coated with at least one of pyrolytic carbon and heparin.

13. A body implantable device of a body compatible material for controlling the size of a fluid flow passageway within the body, which comprises:
   a housing;
   means for securing said housing within the body, said securing means comprising a perforated flange for suturing to a septum;
   a flow passageway extending through said housing;
   signal receiving means, responsive to electromagnetic signals emitted from outside the body and conveyed through the body without wires to said signal receiving means; and
   means for varying the cross section of said flow passageway in a manner responsive to signals received by said signal receiving means.

14. The device of claim 13 in which said means for varying the cross-section of said flow passage way comprises a blade capable of moving transversely across said flow passageway to vary said cross section.

15. The device of claim 14 in which said means for varying the cross-section of said flow passageway comprises a rotatable shaft, and a plurality of blades mounted on said shaft in transverse relation to said passageway, said blades being rotationally spaced about said shaft, with spaces between said blades of at least substantially the fully-open cross-sectional size of said flow passageway, whereby rotation of said shaft causes said blades to sequentially occlude said flow passageway to vary said cross-section thereof.

16. The device of claim 15 in which said shaft is rotated by spring-driven gear means, controlled by said signal receiving means.

17. The device of claim 16 in which said flow passageway is coated with at least one of pyrolytic carbon and heparin.

* * * * *